United States Patent [19]
Caizza et al.

[11] Patent Number: 5,928,215
[45] Date of Patent: Jul. 27, 1999

[54] SYRINGE FILLING AND DELIVERY DEVICE

[75] Inventors: Richard J. Caizza, Barry Lakes, N.J.;
Kris Thiruvillakkat, Cross River, N.Y.

[73] Assignee: Becton, Dickinson and Acompany, Franklin Lakes, N.J.

[21] Appl. No.: 09/090,656

[22] Filed: Jun. 4, 1998

Related U.S. Application Data

[63] Continuation-in-part of application No. 08/911,395, Aug. 14, 1997, Pat. No. 5,807,374.

[51] Int. Cl.$^6$ .................................................. A61M 37/00
[52] U.S. Cl. ............................................ 604/411; 604/414
[58] Field of Search ..................................... 604/411, 164, 604/263, 187, 169, 170, 403, 414, 905

[56] References Cited

U.S. PATENT DOCUMENTS

| | | |
|---|---|---|
| 1,050,043 | 1/1913 | Sellar . |
| 1,501,324 | 7/1924 | Eisele . |
| 1,599,881 | 9/1926 | Eisele . |
| 5,158,554 | 10/1992 | Jepson et al. ............................ 604/283 |
| 5,167,642 | 12/1992 | Fowles .................................... 604/863 |
| 5,171,234 | 12/1992 | Jepson et al. ............................ 604/283 |
| 5,226,900 | 7/1993 | Bancsi et al. ............................ 604/411 |
| 5,322,515 | 6/1994 | Karas et al. ............................. 604/192 |
| 5,382,241 | 1/1995 | Choudhury et al. ..................... 604/192 |
| 5,470,327 | 11/1995 | Helgren et al. .......................... 604/411 |
| 5,483,973 | 1/1996 | Benson et al. ........................... 128/760 |
| 5,501,676 | 3/1996 | Niedospial et al. ..................... 604/283 |
| 5,584,819 | 12/1996 | Kopfer .................................... 604/239 |
| 5,653,698 | 8/1997 | Niedospial et al. ..................... 604/283 |
| 5,755,696 | 5/1998 | Caizza ................................. 604/411 X |
| 5,807,374 | 9/1998 | Caizza et al. ............................ 604/411 |
| 5,820,621 | 10/1998 | Yale et al. ............................... 604/411 |

*Primary Examiner*—John D. Yasko
*Attorney, Agent, or Firm*—John L. Voellmicke

[57] ABSTRACT

A fluid transfer device comprises a shield having an open proximal end, an open distal end and a sidewall therebetween defining a generally hollow cavity. A first cannula assembly including a first cannula connected to a first hub having an open proximal end and a second cannula assembly having a second cannula connected to a second hub having an open proximal end are both positioned at least partially within the cavity of the shield so that the distal end of the first cannula faces the distal end of the second cannula and the first hub and the second hub removably engage opposite ends of the shield so that the open proximal ends of the hubs are accessible for engagement with a syringe.

11 Claims, 13 Drawing Sheets

SYRINGE FILLING AND DELIVERY DEVICE

CROSS-REFERENCE TO RELATED APPLICATIONS

This patent application is a continuation-in-part of U.S. patent application Ser. No. 911,395 filed on Aug. 14, 1997 now U.S. Pat. No. 5,807,374.

FIELD OF THE INVENTION

The subject invention relates to a device mountable on a hypodermic syringe or other fluid delivery device which enables access to medication or other injectable liquid in vials having elastomeric closures and the subsequent delivery of the medication or injectable liquid.

BACKGROUND

A typical hypodermic syringe includes a syringe barrel with a mounting collar for threadedly engaging the hub of a needle assembly. A needle assembly includes a hub and a needle cannula which are connected. In cases where the needle assembly is maintained separately from the syringe until shortly prior to use, the medical practitioner selects an appropriate needle assembly for the procedure being carried out. The needle assembly is removed from its sterile package, and the hub of the needle assembly is threadedly engaged with the mounting collar of the syringe barrel.

Liquid pharmaceuticals and other injectable liquids are often stored in rigid containers which can be accessed using a hypodermic syringe. Some containers for injectable liquids are glass vials with elastomeric closures that can be penetrated by the needle on a hypodermic syringe. To access the liquid in a vial, the plunger of the hypodermic syringe is moved in a proximal direction to draw into the syringe barrel a volume of air substantially equal to the volume of medication that is desired. The sharp distal end of the needle is then urged through the elastomeric closure of the vial, and the air in the syringe barrel is injected into the vial. The distal end of the needle and the vial engaged therewith are then pointed gravitationally upwardly. The practitioner ensures that the distal tip of the needle is covered by the medication in the vial by manipulating the needle and the vial with respect to each other. The plunger of the hypodermic syringe is then moved proximally to draw the desired volume of medication through the needle and into the chamber of the syringe barrel.

After withdrawing a desired volume of medication from a vial, the medical practitioner may inject the medication into either a patient, another vial or an injection site of an intravenous set or catheter. There is a trend toward needleless I.V. systems which do not require a pointed needle cannula to pierce the injection site of an I.V. set. There are systems that have injection sites covered by a pre-slit septum which can be accessed by a blunt cannula. Accordingly, after withdrawing medication from a vial using a sharp needle the user must remove the needle and install a blunt cannula if the medication will be used with an I.V. set having a pre-slit septum.

At the time of prefilling the syringe it may not be known whether medication will be injected through an injection site having a pre-slit septum, which requires a blunt cannula, or through an injection site having a pierceable elastomeric septum which requires a needle assembly having a cannula sharp enough to pierce the septum. In this latter case the practitioner may use the hypodermic needle assembly which was used to fill the syringe.

There is a need for a single device which will allow filling of a syringe from a vial having a pierceable stopper and the subsequent delivery of the medication to an I.V. set through a blunt cannula. There is also a need for a single device which can be used for withdrawing medication from a vial having a pierceable stopper and for injecting this medication through an injection site having a pierceable septum or a pre-slit septum.

SUMMARY OF THE INVENTION

The subject invention relates to a fluid transfer device comprising a shield having an open proximal end, an open distal end and a sidewall therebetween defining a generally hollow cavity. A first cannula assembly including a first cannula having a proximal end, a distal end, and a lumen therethrough, a first hub having an open proximal end and a distal end joined to the proximal end of the first cannula so that the lumen is in fluid communication with the open proximal end of the hub is provided. A second cannula assembly including a second cannula having a proximal end, a distal end and a passageway therethrough, a second hub having an open proximal end and a distal end joined to the proximal end of the second cannula so that the passageway is in fluid communication with the open proximal end of the second hub is also provided. The first cannula assembly and the second cannula assembly are positioned at least partially within the cavity of the shield so that the distal end of the first cannula faces in substantially the opposite direction as the distal end of the second cannula and the first hub and the second hub removably engage opposite ends of the shield so that the open proximal ends of the hubs are accessible for engagement with a fluid transfer device such as a syringe.

A method for transferring an injectable liquid comprising the steps of (a) providing a syringe including a syringe barrel having an elongate cylindrical body defining a chamber for retaining fluid, an open proximal end, a distal end and a tip extending from the distal end having a tip passageway therethrough in fluid communication with the chamber, a stopper in fluid-tight slidable engagement inside the barrel and an elongate plunger rod extending proximally from the stopper through the open proximal end of the barrel;

(b) providing a fluid transfer device including a first cannula assembly including an elongate shield having an open proximal end, an open distal end and a generally hollow cavity therebetween; a first cannula having a proximal end, a distal end and a lumen therethrough, a cutting edge at the distal end of the first cannula for piercing a vial stopper, a first hub having an open proximal end and a distal end joined to the proximal end of the first cannula so that the lumen is in fluid communication with the open proximal end of the first hub; a second cannula assembly including a second cannula having an open proximal end, a blunt distal end and a passageway therethrough, a second hub having an open proximal end and a distal end joined to the proximal end of the second cannula so that the passageway is in fluid communication with the open proximal end of the second hub; the first cannula assembly and the second cannula assembly being positioned at least partially within the cavity of the shield so that the distal end of the first cannula faces the distal end of the second cannula and the first hub and the second hub removably engage opposite ends of the shield so that the open proximal ends of the hubs are accessible for engagement with a syringe;

(c) connecting the fluid transfer device to the syringe so that the tip is positioned within the open proximal end of the first hub and the chamber is in fluid communication with the lumen of the first cannula;

(d) removing the shield from the first cannula assembly;

(e) providing a vial having a pierceable stopper and containing an injectable liquid;

(f) placing the cutting edge of the first cannula in contact with the pierceable stopper;

(g) moving the syringe barrel toward the septum causing the cutting edge on the distal end of the first cannula to pierce the pierceable stopper to establish fluid communication between the interior of the vial and the chamber of the syringe;

(h) withdrawing the desired amount of injectable liquid from the vial into the chamber by moving the plunger rod in a proximal direction with respect to the barrel;

(i) withdrawing the first cannula from the stopper of the vial;

(j) re-installing the shield over the first cannula assembly so that the first cannula is contained within the cavity and applying a force to the shield sufficient to disconnect the first hub from the syringe; and (k) turning the fluid transfer device around and connecting the fluid transfer device to the syringe so that the tip is positioned within the open proximal end of the second hub and the chamber is in fluid communication with the passageway of the second cannula.

DETAILED DESCRIPTION

While this invention is satisfied by embodiments in many different forms, there are shown in the drawings and will be herein described in detail preferred embodiments of the invention with the understanding that the present disclosure is to be considered exemplary of the principles of the invention and not intended to limit the scope of the invention to the embodiments illustrated. The scope of the invention will be measured by the appended claims and their equivalents.

Referring to FIGS. 1—7, a fluid transfer device 20 of the present invention includes a shield 21 having an open proximal end 22, an open distal end 23 and a sidewall 25 therebetween defining a generally hollow cavity 27.

A first cannula assembly 31 includes a first cannula 32 having a proximal end 33, a distal end 34 and a lumen 35 therethrough. A cutting edge 36 is preferably provided at the distal end of the first cannula for piercing a vial stopper or a pierceable septum of an I.V. set injection site. A first hub 37 having an open proximal end 38 and a distal end 39 is joined to the proximal end of the first cannula so that the lumen of the first cannula is in fluid communication with the open proximal end of the first hub.

A second cannula assembly 41 includes a second cannula 42 having a proximal end 43, a distal end 44 and a passageway 45 therethrough. In this embodiment the distal end of the second cannula preferably includes a blunt tip 46. A second hub 47 includes an open proximal end 48 and a distal end 49 joined to the proximal end of the second cannula so that passageway 45 is in fluid communication with the open proximal end of the second hub.

First cannula assembly 31 and second cannula assembly 41 are positioned at least partially within cavity 27 of shield 21 so that the distal end of the first cannula faces in substantially the opposite direction as the distal end of the second cannula and the first hub and the second hub removably engage opposite ends of the shield so that the open proximal ends of the hubs are accessible for engagement with a fluid delivery device such as a syringe. It is within the purview of the present invention to include a shield which holds the first cannula assembly and the second cannula assembly so that the first cannula and the second cannula are parallel to each other rather than facing each other but still facing in substantially opposite direction.

The fluid transfer device of the present invention preferably includes a cap 51 having an open proximal end 52, a distal end 53 and a sidewall 54 therebetween defining a recess 55 in the cap. The cap is removably connected to the distal end of the shield to help protect the open proximal end of the second hub from contamination. As will be described in more detail hereinafter, a cap may also be provided for the proximal end of the shield so that both of the cannula assemblies are protected from contamination by caps.

A fluid transfer device of the present invention is suitable for use with fluid delivery devices such as syringes. For the purpose of illustration, fluid transfer device 20 is connected to a syringe 60 comprising a syringe barrel 61 having a distal end 62, an open proximal end 63 and a circular sidewall 64 defining a chamber 65 for retaining fluid. Volume measuring indicia 67 are on the barrel for measuring the volume of liquid to be delivered. The distal end of the barrel is connected to first hub 37 so that the lumen of first cannula 32 is in fluid communication with chamber 65 of the syringe barrel. In this embodiment, distal end 62 of the syringe barrel includes a frusto-conically shaped tip 68 which engages a frusto-conically shaped surface 40 in open proximal end 38 of the first hub. The distal end of the syringe barrel also preferably, but not necessarily, includes a locking luer-type collar 69 concentrically surrounding tip 68. The luer collar has an internal thread 70 which engages radial projections 58 on first hub 37 to hold it securely to the barrel. In this embodiment second hub 47 of the second cannula assembly also has a frusto-conically shaped surface 50 and radial projections 59 on its open proximal end 48. It is within the scope of the present invention to include various hub configurations which attach to a variety of other medical fluid handling devices. The hub configurations described hereinabove, having a frusto-conically shaped interior, reflects one of these many possibilities. Many syringes and fluid handling devices, such as stopcocks and adapters, and other fluid handling devices contain luer slip and locking luer-type fittings to which a hub having a frusto-conically shaped interior cavity will properly engage.

Figure 1:
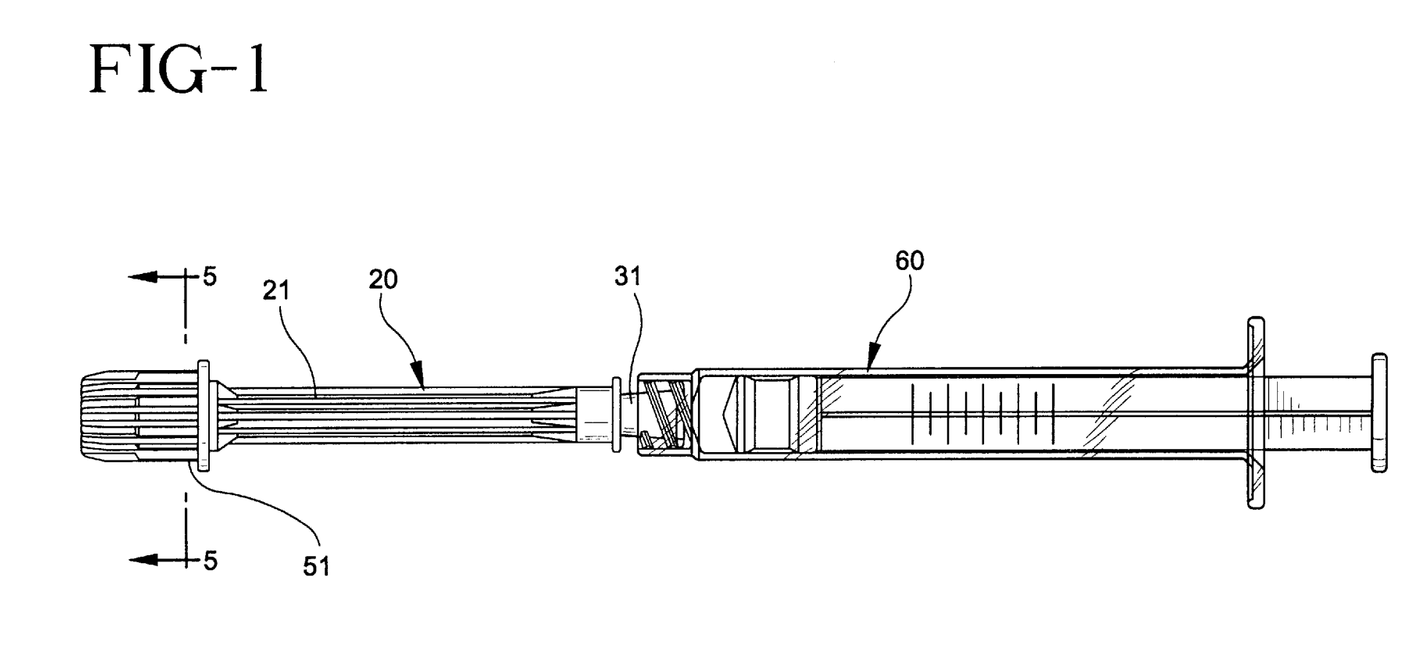
FIG. 1 is a side-elevation view of the fluid transfer device of the present invention attached to a syringe.
Figure 2:
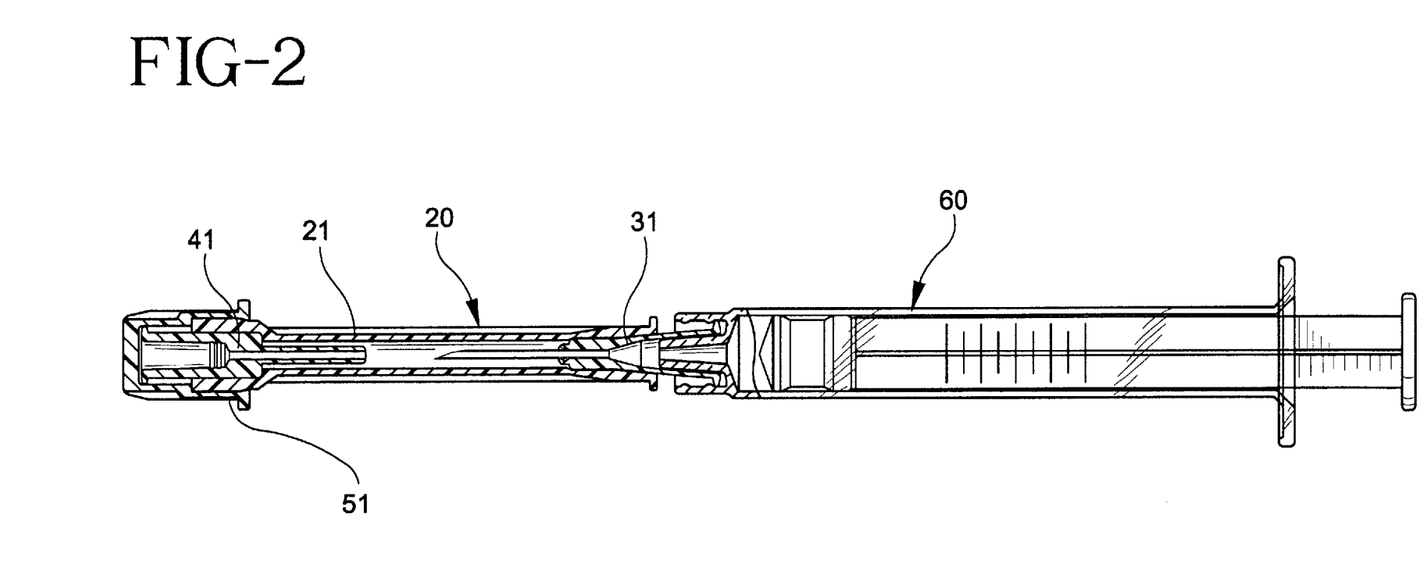
FIG. 2 is a cross-sectional view of the fluid transfer device of FIG. 1.
Figure 3:
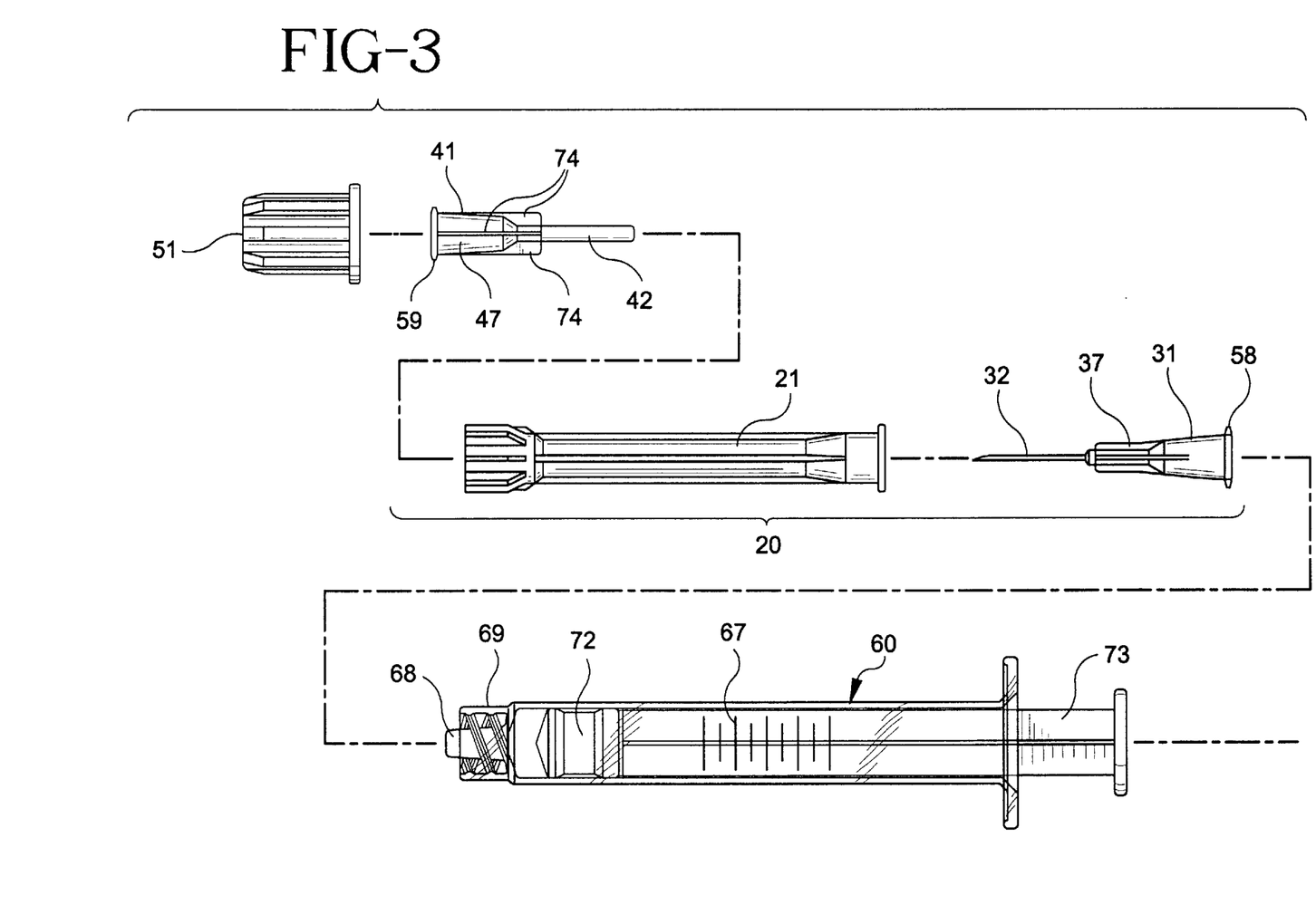
FIG. 3 is an exploded view of the fluid transfer device of the present invention and a syringe.
Figure 4:
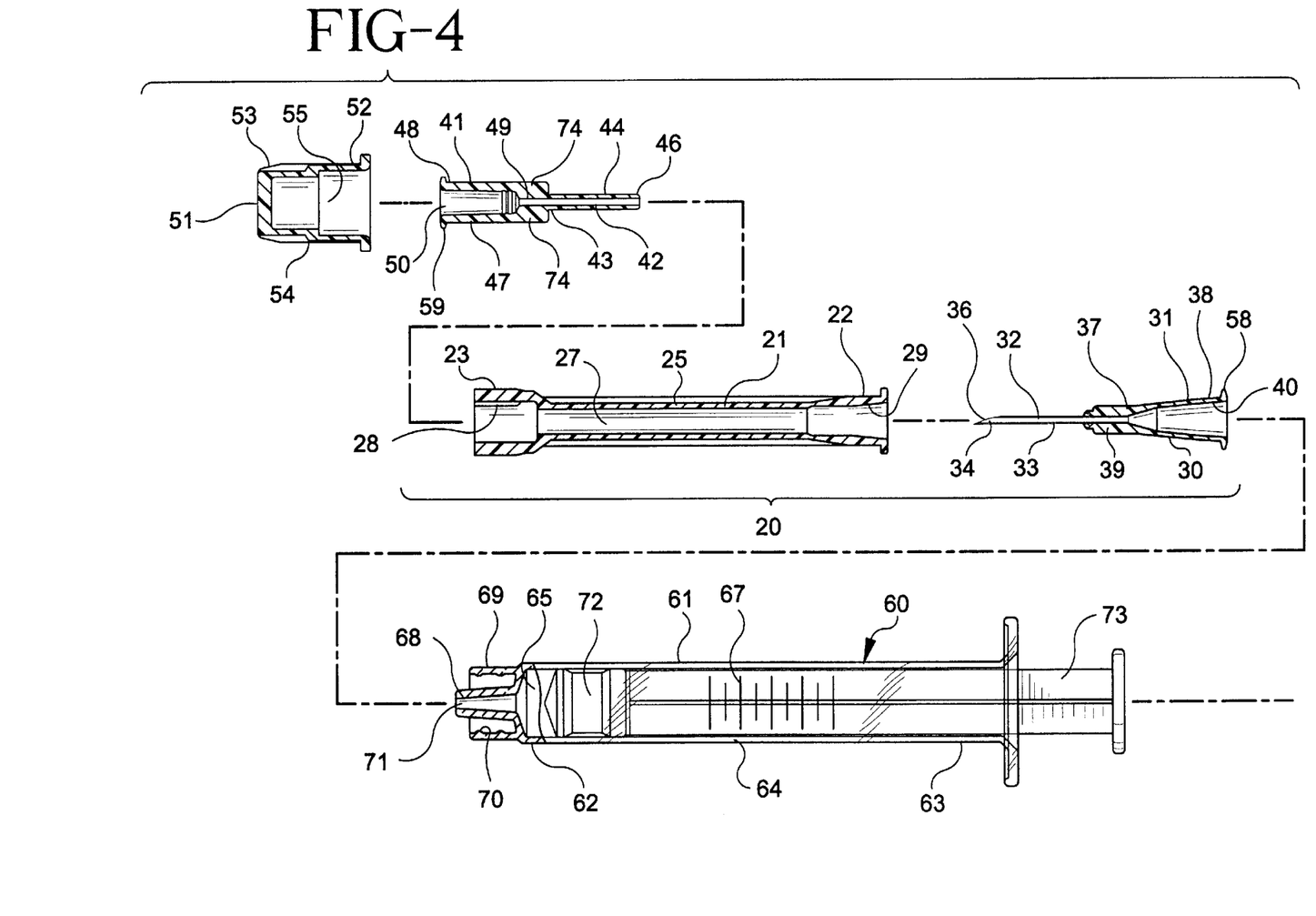
FIG. 4 is a cross-sectional view of the exploded view of the fluid transfer device of FIG. 3.

A stopper 72 is positioned in chamber 65 in sliding fluid-tight engagement with the circular sidewall 64. A rigid elongate plunger rod 73 is connected to the stopper and extends proximally through the open proximal end of the barrel. The stopper and the plunger rod can be made of one-piece unitary construction. Force applied to the plunger rod causing sliding movement of the stopper in a proximal direction draws fluid through conduit 71 in the tip and into chamber 65. Conversely, sliding movement of stopper 72 in a distal direction urges fluid from chamber 65 through conduit 71.

Figure 5:
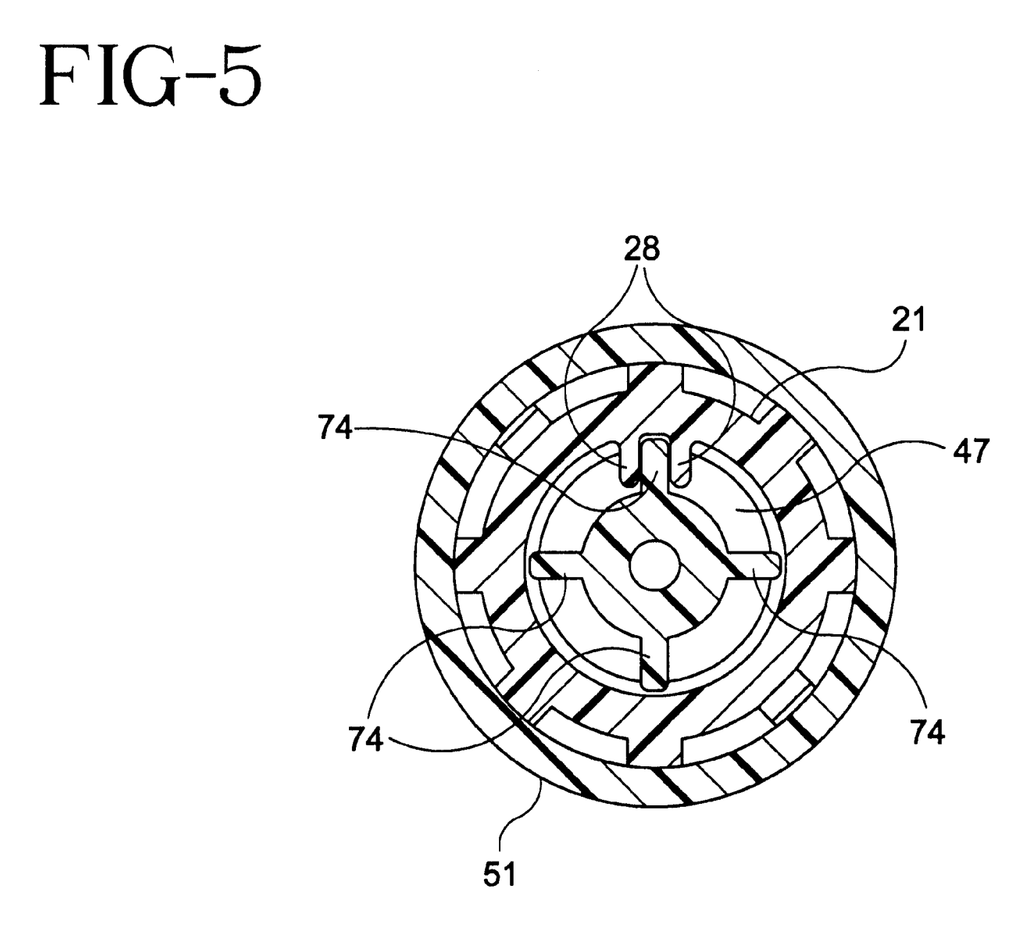
FIG. 5 is a cross-sectional view of the fluid transfer device of FIG. 1 taken along line 5—5.

When mounting fluid transfer device 20 to a syringe such as syringe 60 having a locking luer-type collar, the fluid transfer device is rotated to advance projections 58 on hub 37 along internal thread 70 of collar 69. The rotation will pull the hub toward the syringe barrel tightly engaging tip 68 of the syringe barrel into the open proximal end of hub 37. Because of the torque required to engage the fluid transfer device to a syringe barrel having a locking luer-type collar is desirable to have torque transmitting means for allowing rotational force applied to the shield to be transmitted to the hub of the first needle assembly and also to the hub of the second needle assembly. The means for transmitting torque can include frictional engagement between the exterior of the hub and the cavity in the shield. For example, inside surface 29 of the cavity can be tapered at the same angle as the outside surface 30 of the first hub promoting a greater area for frictional engagement. Therefore, pushing on the shield while engaging or disengaging a needle assembly from a syringe having a locking luer-type collar will increase the frictional engagement between the hub and the sleeve and allow the rotational force to be transmitted from the shield to the hub. In this embodiment, as best illustrated in FIG. 5 additional structure is provided to help transmit rotational force between the shield and the second cannula assembly. To improve the ability to transmit rotational forces from the shield to the second hub one or more protuberances on the hub such as axial ribs 74 which engage a slot in shield 21 formed by projections 28 in the shield cavity. Any combination of protuberances and/or recesses on the hub or housing which are capable of transmitting sufficient torque to engage the hub to the syringe barrel are satisfactory for functioning as torque transmitting structure along with carefully designed surfaces which can transmit torque through frictional forces.

Fluid transfer device 20 of the present embodiment coupled with a fluid delivery device, such as a syringe 70, can be used to access fluid in a vial having a pierceable stopper and deliver the fluid to an injection site on an I.V. set or catheter regardless of whether the injection site has a pre-slit septum or a pierceable septum. This is a major advantage of the present invention. The present embodiment contains a blunt cannula and cannula having a cutting edge at its distal end which is sharp enough to pierce rubber stoppers and septums but does not have to be and is preferably not sharp enough for injection through the skin.

Figure 6:
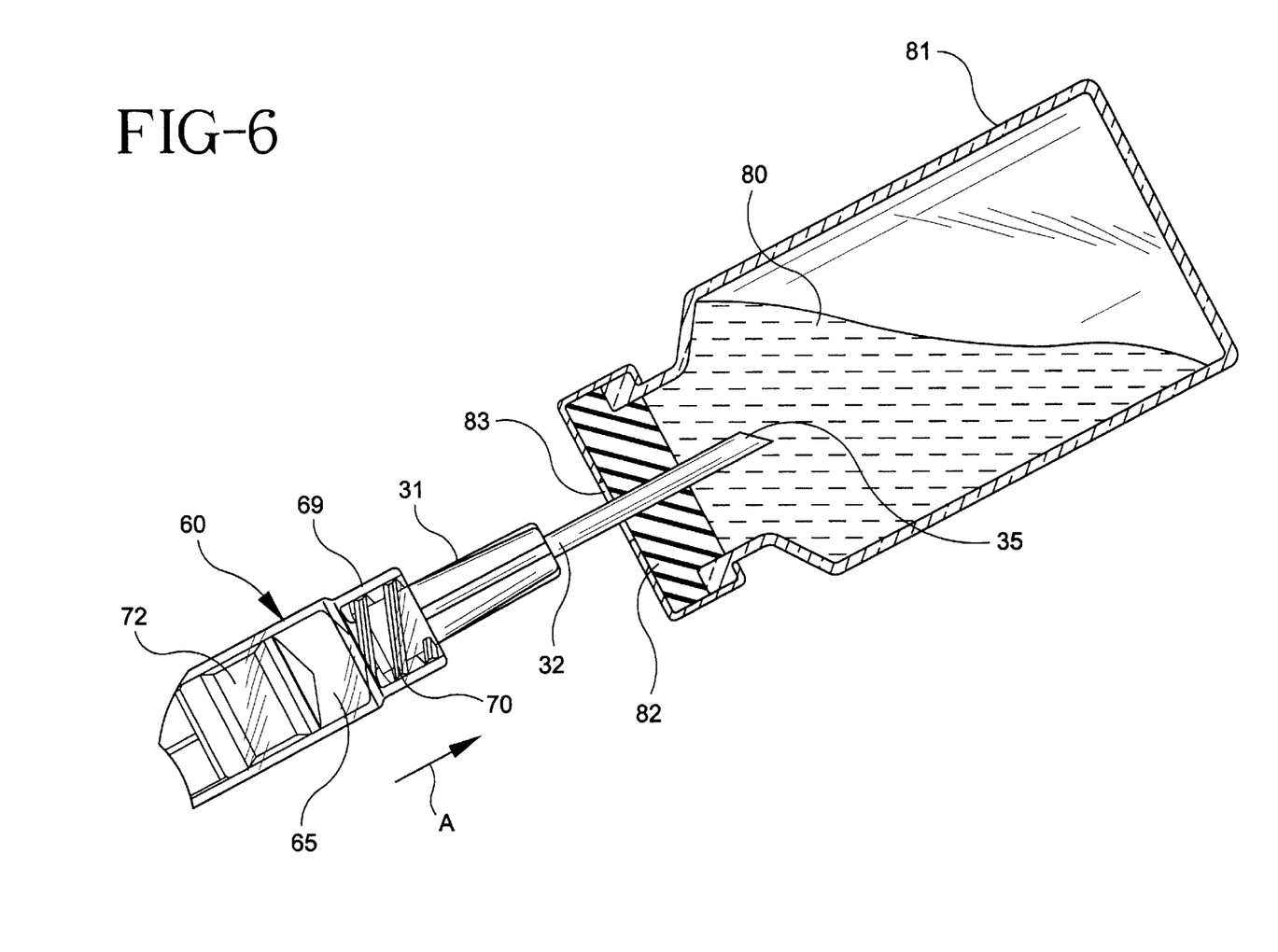
FIG. 6 is a side-elevational view of a component of the fluid transfer device and syringe being used to draw liquid from a stoppered vial.

As best illustrated in FIG. 6, fluid transfer device 20 can be used with syringe 60 to access injectable liquid or medication, such as fluid 80 contained in vial 81 having a pierceable stopper 82. The first step is to connect the fluid transfer device 20 to syringe 60 so that tip 68 is positioned within the open proximal end of first hub 37 and chamber 65 is in fluid communication with the lumen of the first cannula. To accomplish this result, a rotational force is applied to the shield which causes the hub to rotate and projections 58 on the hub to follow internal thread 70 in the locking collar. When the first cannula is securely attached to the syringe, the user can pull on the shield to disengage the shield form the first cannula assembly. The fluid in the vial is accessed by placing the cutting edge of the first cannula on top surface 83 of stopper 82 and applying an axial force through the syringe barrel in direction A. The cutting edge on the first cannula will pierce the stopper and allow fluid communication between the interior of the vial and the chamber of the syringe. At this point, liquid can be drawn into the syringe barrel using known methods such as the method described hereinabove. The syringe and the first cannula assembly are then withdrawn from the stopper of the vial. The shield of the fluid transfer device may now be re-engaged with the hub of the first cannula assembly to protect the first cannula assembly from contamination.

Figure 7:
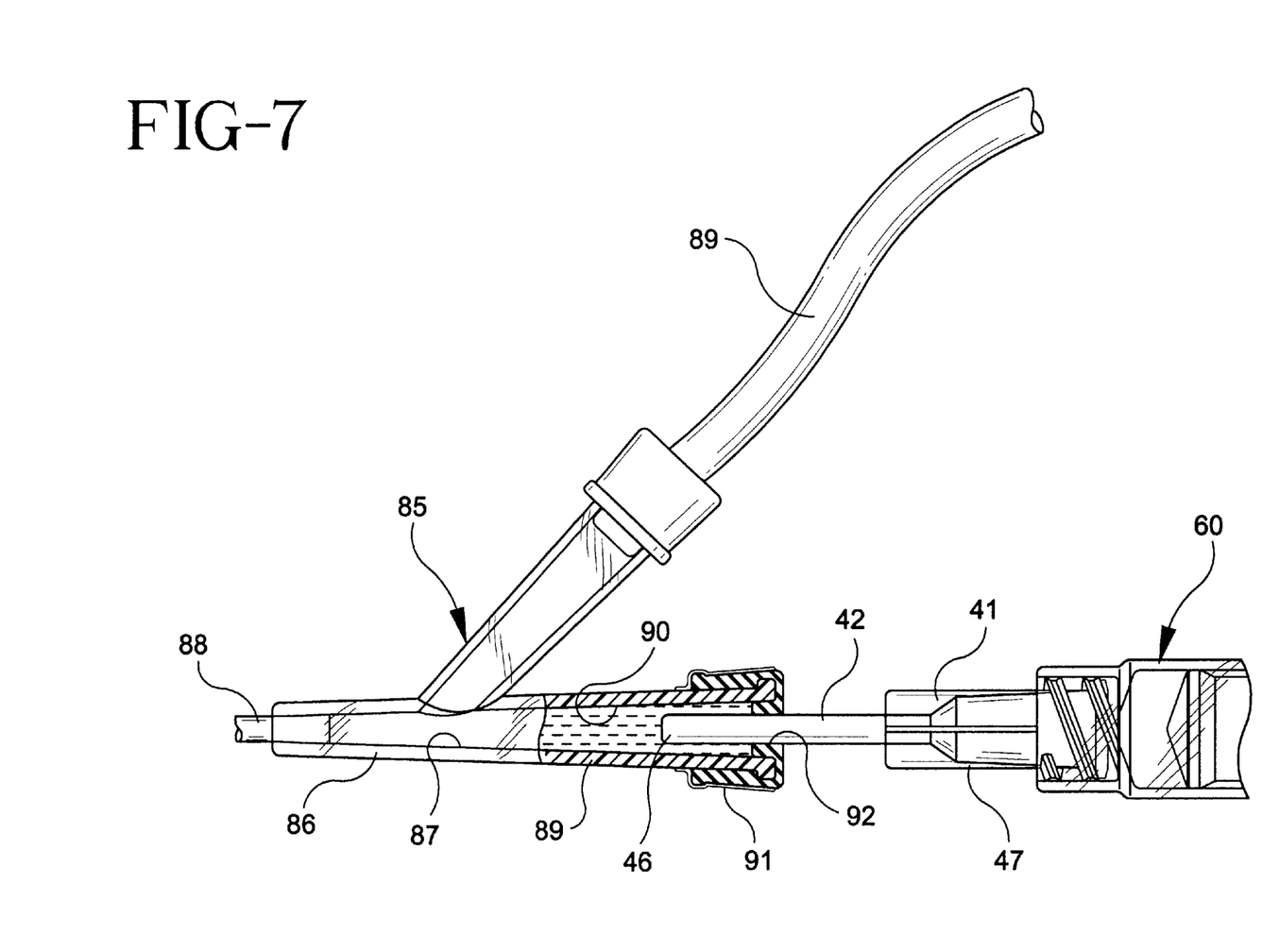
FIG. 7 is a side-elevational view illustrating a component of the fluid transfer device and syringe being used to inject liquid into an injection site of an I.V. set.

The filled syringe 60 with fluid transfer device 20 attached is transferred to the point of use where it can be used to inject fluid into a patient through an I.V. set or a catheter having an injection site with a pre-slit or pierceable septum. Specifically, as illustrated in FIG. 7, an I.V. set 85 can include a housing 86 having a hollow interior conduit 87 and a flexible tube 88 connected to the vascular system of a patient, usually through a catheter. Housing 86 also includes another flexible tube 89 which is connected to a source of I.V. fluid. Housing 86 also includes port 89 having a conduit 90 therethrough in communication with the interior conduit 87. A pre-slit septum 91 covers the open end of conduit 90. The most common ports are covered by pierceable septums or pre-slit septums and are known in the art and sometimes referred to as "PRN" from the Latin pro re nata meaning"as the need arises". Septum 91 is a pre-slit septum having a slit 92 therein. Septum 91 effectively seals conduit 90 from the exterior of the housing.

At this point, the user applies a rotational force to the shield of the fluid transfer device to disengage the first cannula assembly from the syringe. If the fluid transfer device contains a removable cap over its distal end, the cap is now removed. The user now turns the fluid transfer device around and connects the fluid transfer device to the syringe so that the tip of the syringe barrel is positioned within the open proximal end of second hub 47 and the chamber is in fluid communication with the passageway of second cannula 42. In this embodiment, the connection is accomplished by applying a rotational force to the shield to engage the second hub securely to the syringe barrel, as described hereinabove. The shield is now removed from second cannula assembly 41 by applying an axial force to disengage it from the second hub. The user now moves the syringe and the second cannula assembly to an I.V. assembly set having an injection site with a pre-slit septum and advances the syringe toward the pre-slit septum so that the blunt tip of the second cannula passes through the slit in the septum and establishes fluid communication with the I.V. set, as best illustrated in FIG. 7. The plunger can now be advanced so that the stopper moves fluid from the chamber through the passageway of the second cannula and into the I.V. set.

If the septum of the I.V. set is pierceable and not pre-slit, the user does not have to disengage the first cannula assembly from the syringe and install the second cannula assembly. The method would consist of filling the syringe as described hereinabove, preferably re-applying the shield to the first cannula assembly to protect the second cannula during transfer of the syringe and fluid transfer device to the injection site, as described hereinabove for the pre-slit septum. The user then removes the shield from the first cannula assembly and advances the syringe toward the septum so that the cutting edge of the first cannula pierces the septum and establishes fluid communication with the I.V. set. Greater force will be required to penetrate a pierceable septum and the sharp cutting edge of the first cannula will be necessary since this procedure cannot be accomplished with a blunt cannula. Accordingly, the fluid transfer device of the present invention allows the filling of a syringe from a vial having a pierceable stopper and delivering this fluid through an I.V. site having a pre-slit or pierceable septum. No other apparatus is necessary to accomplish this result.

Figure 8:
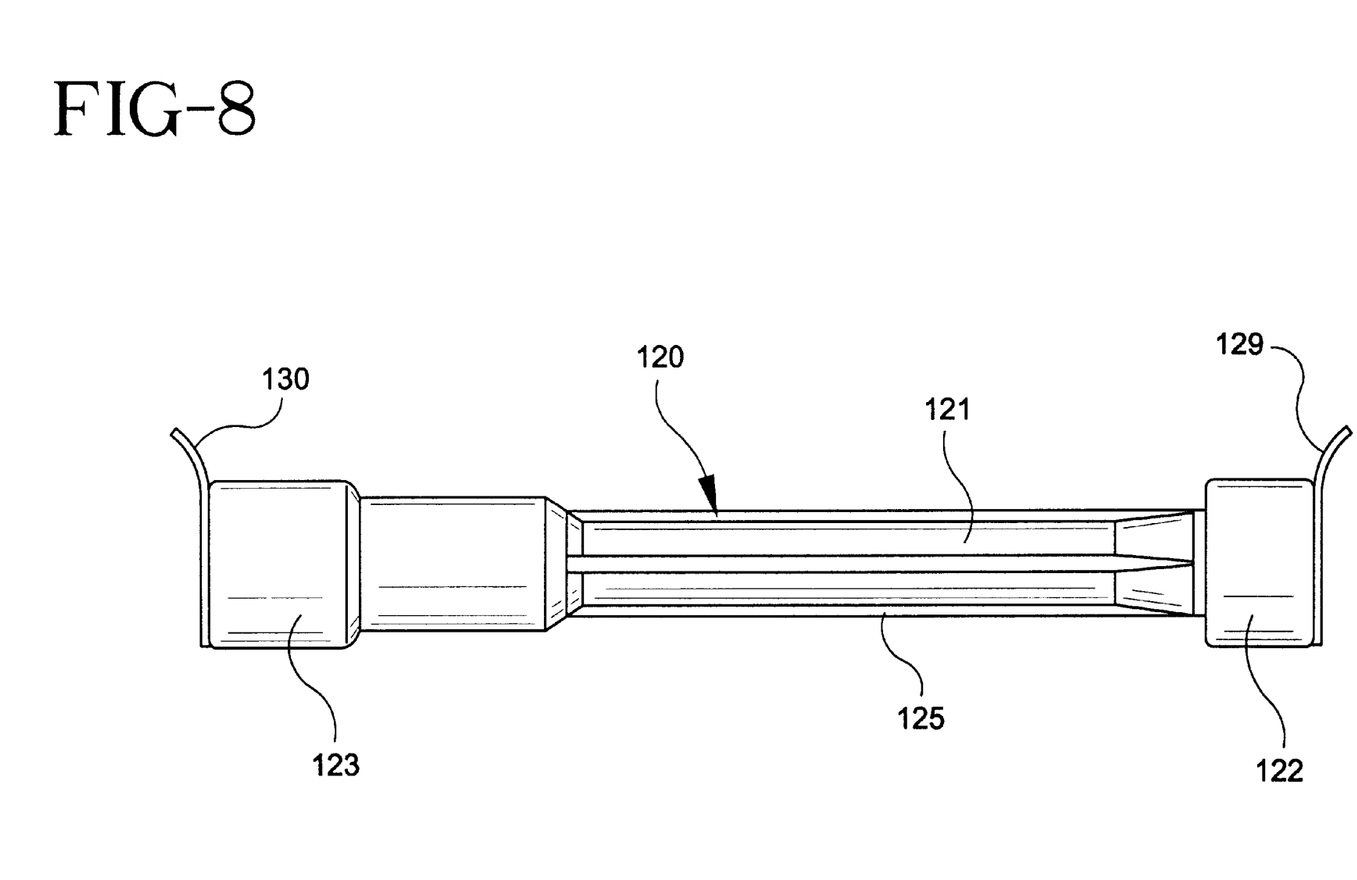
FIG. 8 is a side-elevational view of an alternative fluid transfer device of the present invention.
Figure 9:
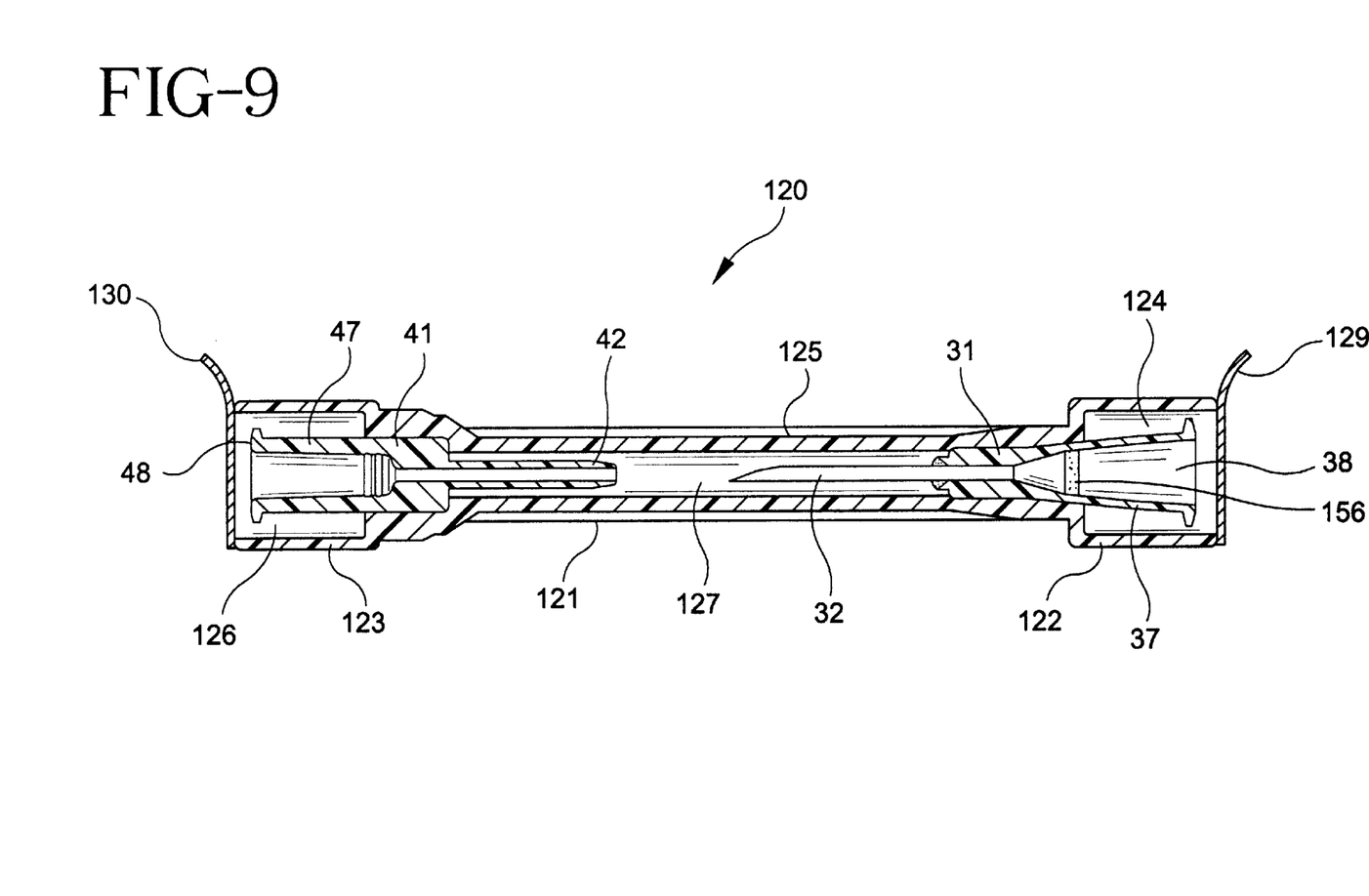
FIG. 9 is a cross-sectional view of the fluid transfer device of FIG. 8.

FIGS. 8–9 illustrate an alternative embodiment of the present invention. An alternative fluid transfer device 120 includes a shield 121 having an open proximal end 122, an open distal end 123 and a sidewall 125 therebetween defining a generally hollow cavity 127. Fluid transfer device 120 also includes a first cannula assembly 31 having a first cannula 32 and a first hub 37, and a second cannula assembly 41 having a second cannula 42 and a second hub 47. First hub 37 has an open proximal end 38 and second hub 47 has an open proximal end 48. Cavity 127, at proximal end 122 of the shield, is enlarged to form a proximal receptacle 124 which is larger than first hub 37 so that the first hub is contained completely within the proximal receptacle 124 portion of the cavity. Also, distal end 123 of the shield is enlarged so that cavity 127 forms a distal receptacle 126 which is larger than second hub 47 so that the second hub is contained within distal receptacle 126 portion of the cavity. The receptacles are large enough so that the fluid transfer device can be attached to a hypodermic syringe through either the open proximal end or the open distal end of the shield. However, in this embodiment, the cannula assemblies cannot be removed from the shield by hand since digital access is substantially restricted.

A tab 129 is removably sealed over open proximal end 122 of the shield for protecting open proximal end 38 of the first hub from contamination. Also, a tab 130 is removably sealed over open distal end 123 of the shield for protecting open proximal end 48 of the second hub from contamination. Tabs 129 and 130 can be of the peel-off variety which are heat sealed across the open ends of the shield. Tabs may contain or be made of an air-permeable material capable of filtering out bacteria. The tabs may also be made of material that is not air-permeable. The sterilization process and other design factors will determine the choice of tab material.

In this embodiment, first hub 37 includes a filter 56 for filtering liquid passing between the lumen and the open proximal end of the first hub. The filter can be helpful in filtering debris that may be contained in the fluid storage container so that the debris is not drawn into the chamber of the syringe barrel.

Figure 10:
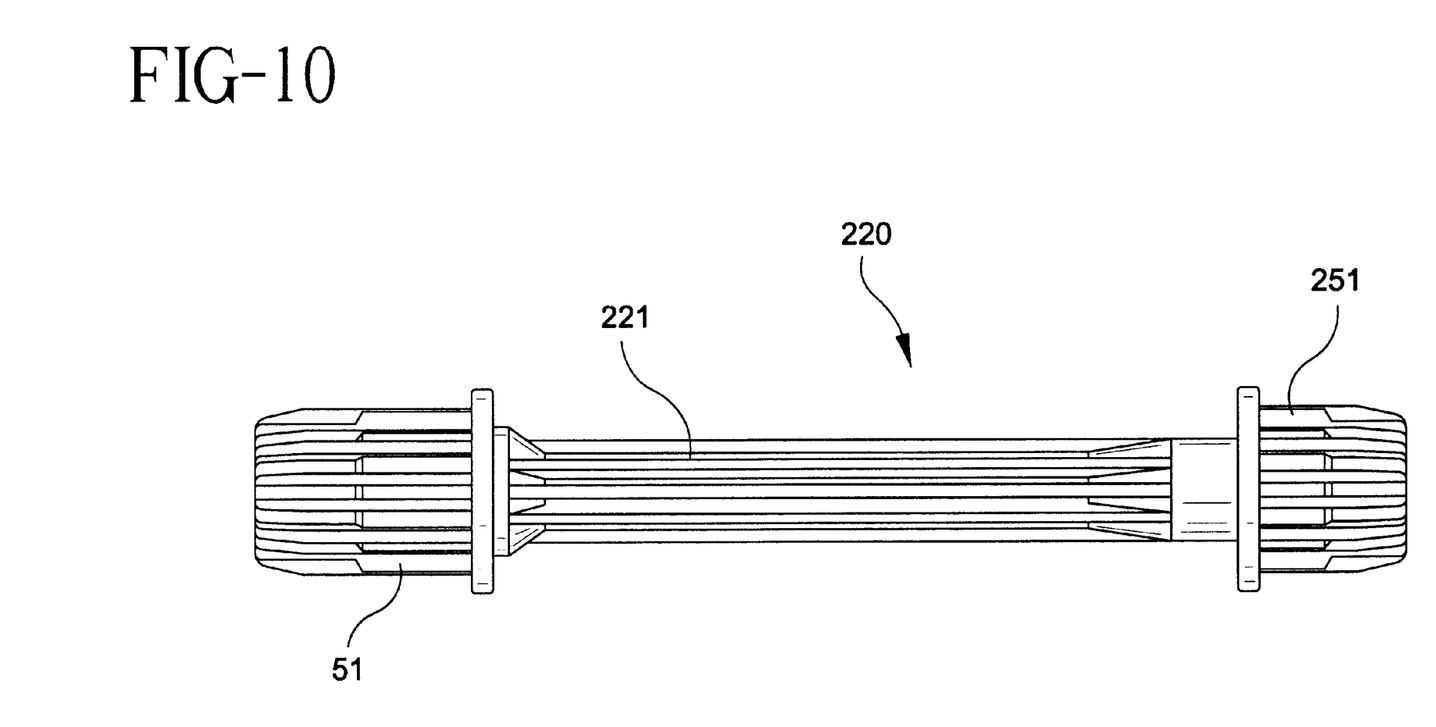
FIG. 10 is a side-elevational view of another alternative fluid transfer device of the present invention.
Figure 11:
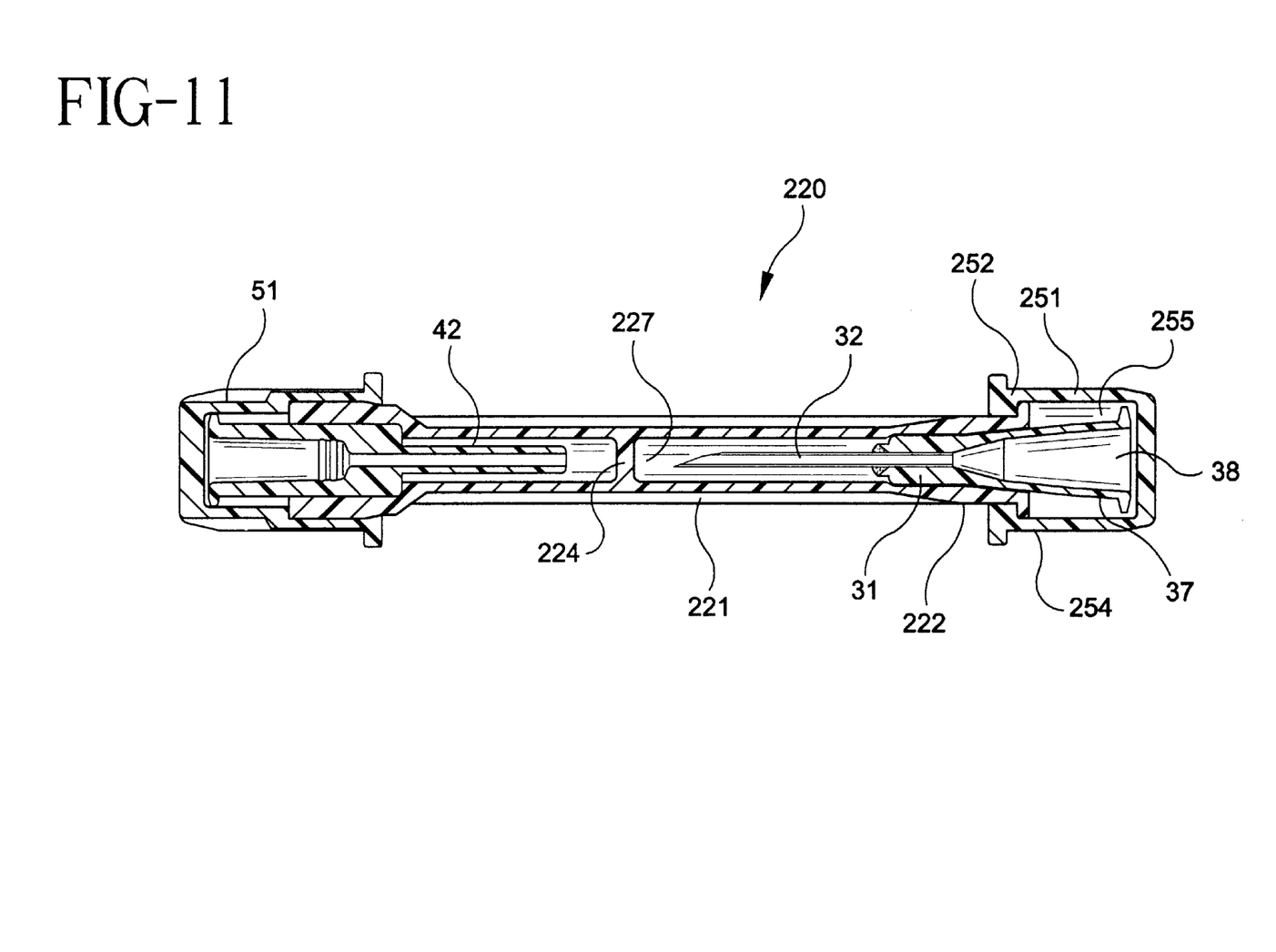
FIG. 11 is a cross-sectional view of the fluid transfer device of FIG. 10.

FIGS. 10–11 illustrate another alternative fluid transfer device 220. The embodiment of FIGS. 10–11 is similar to the embodiment of FIGS. 1–7. Fluid transfer device 220 further includes an additional cap 251 having an open proximal end 252, a distal end 253 and a sidewall 254 therebetween defining a recess 255. Cap 251 is removably connected to open proximal end 222 of shield 221 to protect open proximal end 38 of first hub 37 from contamination. Shield 221 also includes a barrier 224 separating the portion of cavity 227 containing first cannula 32 from the portion of cavity 227 containing second cannula 42. Under certain circumstances barrier 224 may be helpful to further protect the unopened end of the fluid transfer device from contamination through the open end.

It should be noted that various structures for the shield of the fluid transfer device of the present invention are taught. For example, there are embodiments having a cap over one or both of the open ends of the shield, there are embodiments having peel-tabs over the open proximal ends of the shield, and there are embodiments having neither caps nor tabs. There are embodiments having the hub exposed or contained within a recess formed at an enlarged open end of the shield. These features can be mixed and matched to suit the various applications for using the fluid transfer device of the present invention. For example, both ends of the shield can be enlarged to form a recess to cover the hubs with one end being covered by a cap and the other end being covered by a removable tab. All of these various combinations are within the purview of the present invention. Likewise, although the first cannula is shown as a slightly sharpened distal end suitable for puncturing septums but not for skin injection and the second cannula is shown as a blunt cannula these limitations do not restrict the present invention. Both cannula can have very sharp tips suitable for through-the-skin injection. Also, the second cannula can be a sharp through-the-skin injection cannula so that the filling procedure can be carried out with the less sharp first cannula and the sharper cannula only exposed at the time of injection. Again, all these combinations are within the purview of the present invention.

Figure 12:
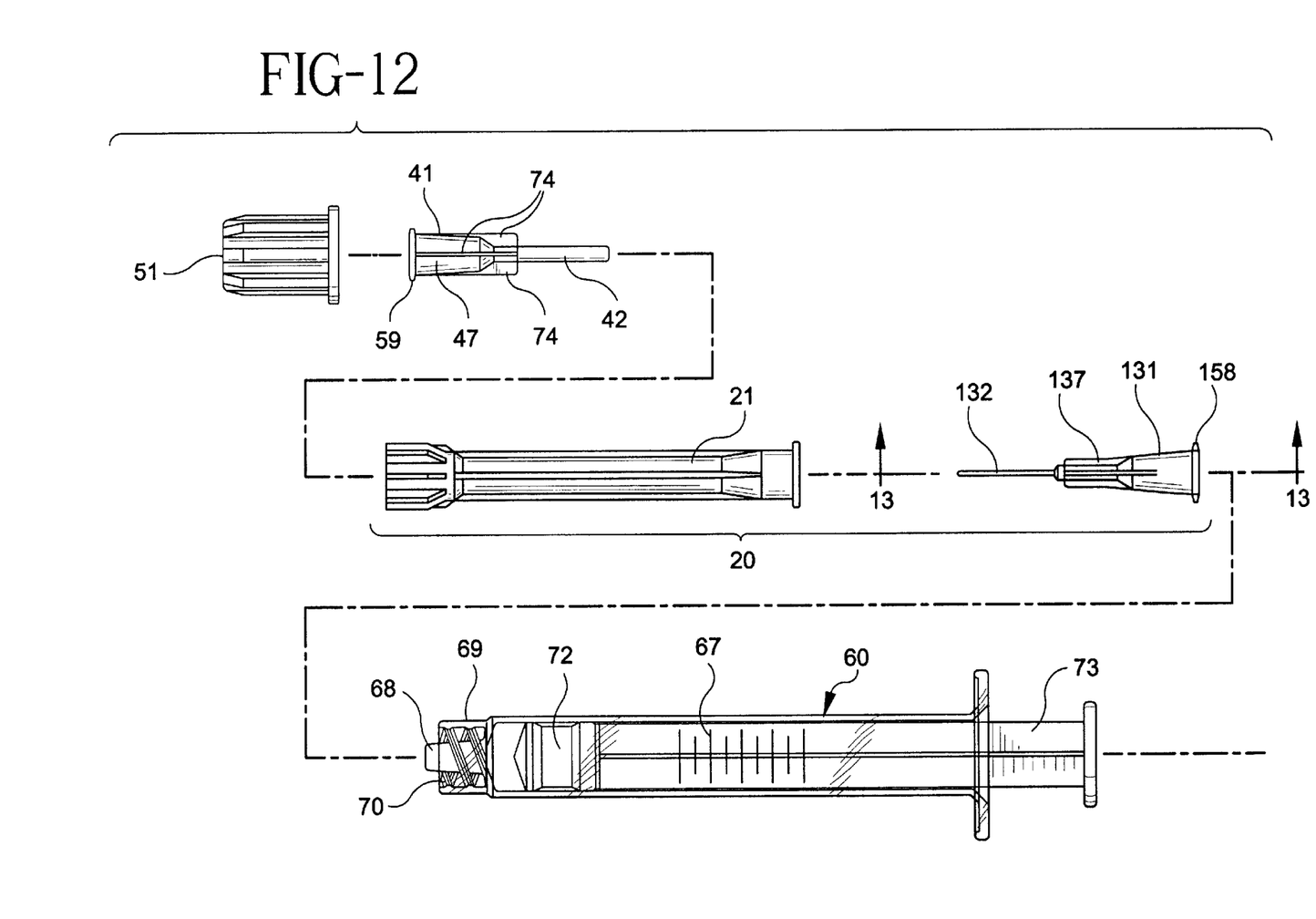
FIG. 12 is an exploded view of an alternative fluid transfer device of the present invention and a syringe.
Figure 13:
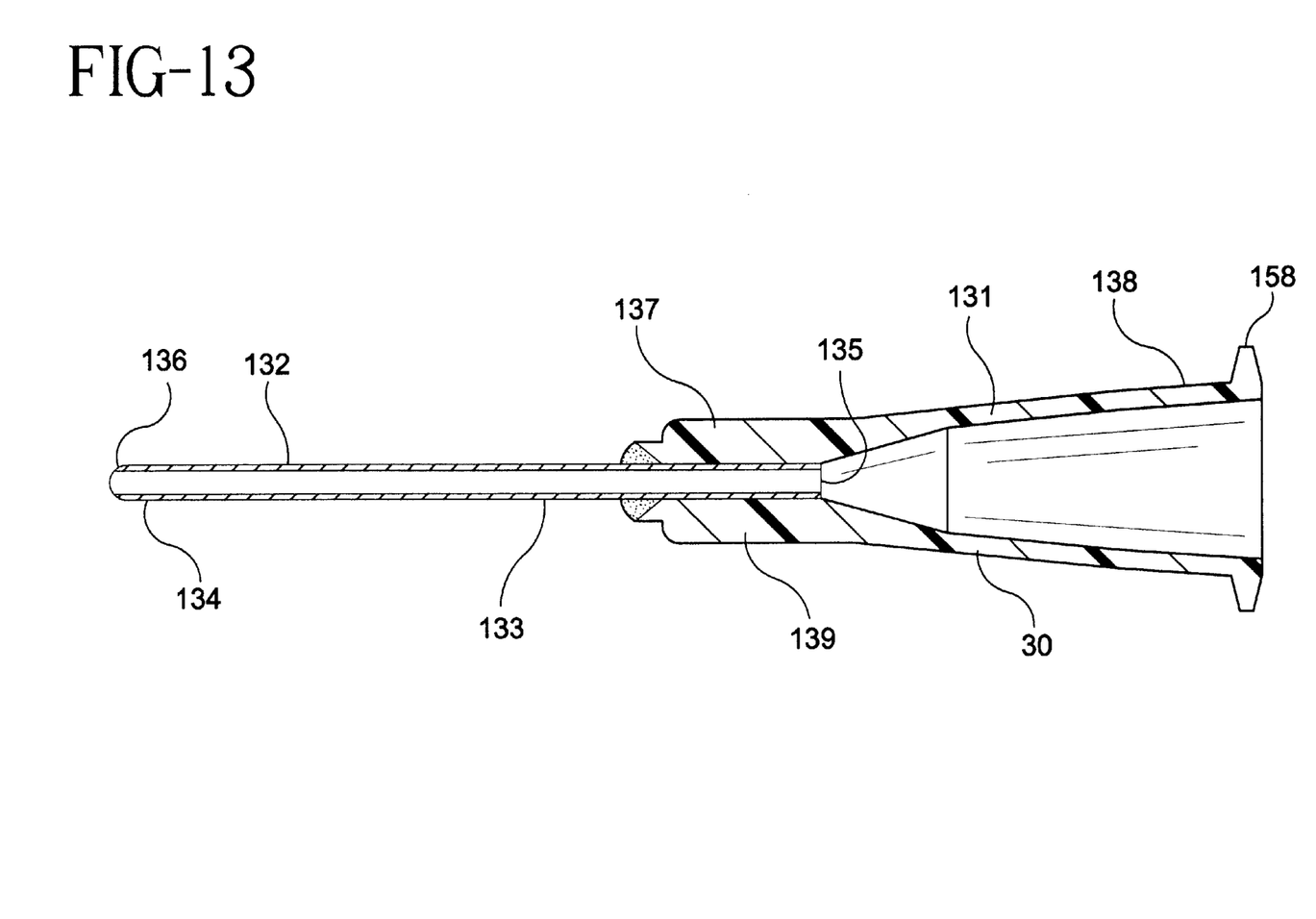
FIG. 13 is a cross-sectional view of the first cannula assembly of FIG. 12 taken along line 13—13.

FIGS. 12–13 illustrate another alternative embodiment of the present invention. This embodiment is similar to the embodiment of FIGS. 1–5 except that the first cannula assembly includes a blunt cannula. Specifically, a first cannula assembly 131 includes a first cannula 132 having a proximal end 133, a distal end 134 and a lumen 135 therethrough. In this embodiment the distal end of the first cannula includes a blunt tip 136. A first hub 137 having an open proximal end 138 and a distal end 139 is joined to the proximal end of the first cannula so that the lumen of the first cannula is in fluid communication with the open proximal end of the first hub.

In this embodiment both first cannula assembly 131 and second cannula assembly 41 include cannula having blunt distal ends. The present invention includes blunt cannulas having open distal ends such as first cannula 132 and second cannula 42 where the lumen passes directly out the distal end. It is within the purview of the present invention to include blunt cannulas having blunt distal ends wherein the end of the cannula is closed and fluid enters and exits the lumen through one or more apertures in the side of the cannula. Blunt cannulas are cannulas having variously shaped distal ends which are designed specifically to avoid accidental skin puncture during normal use. Blunt cannulas are designed to work in conjunction with injection sites having pre-slit septums. Accordingly, blunt cannulas can be shaped in any fashion that will facilitate use with pre-slit septums and still resist accidental skin puncture during normal use.

The present embodiment is suitable for use wherein the source of liquid which will be drawn into the syringe is accessible through a pre-slit septum. In use, the fluid transfer device is connected to syringe 60 so that tip 68 is positioned within open proximal end 138 of the hub and chamber 65 is in fluid communication with the lumen of the first cannula. To accomplish this result, a rotational force is applied to shield 21 which causes the hub to rotate and projections 158 on the hub to follow internal threads 70 in the locking collar. When the first cannula is securely attached to the syringe, the user can pull on the shield to disengage the shield from the first cannula assembly. Fluid in a vial or other receptacle having a pre-slit septum is accessed by advancing the syringe toward the pre-slit septum so that the blunt tip of the first cannula passes through the slit in the septum and establishes fluid communication with the fluid therein (receptacle not illustrated). At this point, liquid can be drawn into the syringe barrel using known methods. The syringe and the first cannula assembly are then withdrawn from the pre-slit septum of the vial. The shield of the transfer device is now re-engaged with the hub of the first cannula assembly to protect the first cannula assembly from contamination.

The syringe filling device including the second cannula assembly can now be used as described hereinabove for transferring injectable liquid into an injection site having a pre-slit septum.

Having blunt cannula in both cannula assemblies allows withdrawing liquid from vials or other receptacles having a pre-slit septum and subsequently replacing the first cannula assembly with the second cannula assembly when delivering injectable liquid through an injection site having a pre-slit septum. Accordingly, a clean unused blunt cannula will be provided at the time of delivery of the liquid to the patient.

It is also within the purview of the present invention to modify the embodiment of FIGS. 8 and 9 and the embodiment of FIGS. 10 and 11 to include a first cannula having a blunt distal end.

What is claimed is:

1. A fluid transfer device comprising:

shield having an open proximal end, an open distal end and a sidewall therebetween defining a generally hollow cavity;

a first cannula assembly including a first cannula having a proximal end, a blunt distal end and a lumen therethrough, a first hub having an open proximal end and a distal end joined to said proximal end of said first cannula so that said lumen is in fluid communication with said open proximal end of said first hub;

a second cannula assembly including a second cannula having a proximal end, a blunt distal end and a passageway therethrough, a second hub having an open proximal end and a distal end joined to said proximal end of said second cannula so that passageway is in fluid communication with said open proximal end of said second hub;

said first cannula assembly and said second cannula assembly being positioned at least partially within said cavity of said shield so that said distal end of said first cannula faces in substantially the opposite direction as said distal end of said second cannula and said first hub and said second hub removably engage opposite ends of said shield so that said open proximal ends of said hubs are accessible for engagement with a fluid delivery device.

2. The fluid transfer device of claim 1 further including a cap having an open proximal end, a distal end and a sidewall therebetween defining a recess in said cap, said cap being removably connected to said distal end of said shield to protect the open proximal end of said second hub from contamination.

3. The fluid transfer device of claim 1 further including a cap having an open proximal end, a distal end and a sidewall therebetween defining a recess in said cap, said cap being removably connected to said proximal end of said shield to protect the open proximal end of said first hub from contamination.

4. The fluid transfer device of claim 1 wherein said cavity at said open distal end of said shield is larger than said second hub so that said second hub is contained in said cavity.

5. The fluid transfer device of claim 4 further including a tab removably sealed to said open distal end of said shield for protecting the open proximal end of said second hub from contamination.

6. The fluid transfer device of claim 1 wherein said cavity at said open proximal end of said shield is larger than said first hub so that said first hub is contained in said cavity.

7. The fluid transfer device of claim 6 further including a tab removably sealed to the open proximal end of said shield for protecting the open proximal end of said first hub from contamination.

8. The fluid transfer device of claim 1 wherein said cavity in said shield contains a barrier separating the portion of said cavity containing said first cannula from the portions of said cavity containing said second cannula.

9. The fluid transfer device of claim 1 further including a filter in said first hub for filtering liquid passing between said lumen and said open proximal end of said first hub.

10. The fluid transfer device of claim 1 further including a syringe barrel having an elongate body defining a chamber for retaining fluid, an open proximal end, a distal end and a tip extending from the distal end having a tip passageway therethrough in fluid communication with said chamber, said tip being positioned within said open proximal end of said first hub so that said chamber is in fluid communication with said lumen.

11. The fluid transfer device of claim 10 further including a stopper in fluid-tight engagement inside said barrel, and a rigid elongate plunger rod extending proximally from said stopper through said open proximal end of said barrel.

* * * * *